United States Patent [19]

Newman et al.

[11] 4,427,783
[45] Jan. 24, 1984

[54] IMMUNOASSAY OF THYMOSIN $\alpha_1$

[75] Inventors: Edward Newman, West Orange; A. Hirotoshi Nishikawa, West Caldwell; Herbert E. Spiegel, Cedar Grove; Julia Symington, Passaic, all of N.J.

[73] Assignee: Hoffmann-La Roche Inc., Nutley, N.J.

[21] Appl. No.: 330,402

[22] Filed: Dec. 14, 1981

[51] Int. Cl.³ .................... G01N 33/54; G01N 33/56; G01N 33/74
[52] U.S. Cl. .................... 436/542; 436/543; 436/544; 436/545; 436/547; 436/804; 436/817; 436/811; 260/112 B; 435/4; 435/7
[58] Field of Search ................ 424/1, 1.5; 260/112 R; 436/518–536, 538, 542; 23/920; 435/4, 7

[56] References Cited

U.S. PATENT DOCUMENTS

| | | | |
|---|---|---|---|
| 4,010,148 | 3/1977 | Goldstein | 260/112 R |
| 4,055,633 | 10/1977 | Goldstein | 424/1 |
| 4,079,127 | 3/1978 | Goldstein et al. | 424/177 |
| 4,082,737 | 4/1978 | McGregor et al. | 260/112.5 R |
| 4,264,571 | 4/1981 | Goldstein et al. | 424/1 |
| 4,339,427 | 7/1982 | Goldstein et al. | 424/1 |

Primary Examiner—Benjamin R. Padgett
Assistant Examiner—M. Moskowitz
Attorney, Agent, or Firm—Jon S. Saxe; Bernard S. Leon; George M. Gould

[57] ABSTRACT

An improved immunoassay for the polypeptide hormone thymosin $\alpha_1$ is described. The assay employs an improved antibody which is elicited by an immunogen which has been prepared by coupling [Tyr¹]-thymosin $\alpha_1$ to an immunogenic carrier protein using a bifunctional diazonium coupling agent.

16 Claims, No Drawings

IMMUNOASSAY OF THYMOSIN $\alpha_1$

BACKGROUND OF THE INVENTION

Thymosin $\alpha_1$ is a heat stable, acidic polypeptide composed of 28 amino acid residues. This thymic hormone has been isolated from calf thymus fraction 5 and its amino acid sequence determined. Thymosin $\alpha_1$ is one of several polypeptides present in thymosin fraction 5 which participate in the regulation, differentiation and function of thymic dependent lymphocytes (T-cells). The isolation, characterization and use of thymosin $\alpha_1$ is described in greater detail in U.S. Pat. No. 4,079,127.

An immumoassay for a polypeptide hormone of the thymus known as thymopoietin or thymin is disclosed in U.S. Pat. No. 4,055,633. In particular, this patent discloses a radioimmunoassay for thymopoietin utilizing an antibody elicited by an immunogen comprising purified thymopoietin covalently coupled to an immunogenic carrier material such as bovine gamma globulin using glutaraldehyde as the coupling agent. The labelled antigen used in the assay is preferably $^{125}$I-thymopoietin.

It should be noted that thymopoietin is totally non-analogous to thymosin $\alpha_1$ in structure, amino acid composition and sequence, biological activity profile, physical properties and immunological properties.

A radioimmunoassay for a partially purified thymosin fraction, i.e., thymosin fraction 6, which is now known to contain a mixture of a number of polypeptides, is reported by Schulof et al., Fed. Proc. 32, 962 (1973). See also Goldstein et al., Fed. Proc. 33, 2053 (1974).

U.S. Patent Application Ser. No. 4,971, now U.S. Pat. No. 4,264,571, filed Jan. 22, 1979 describes a radioimmunoassay for thymosin $\alpha_1$. This assay employs an antibody elicited by an immunogen comprising thymosin $\alpha_1$ covalently linked to hemocyanin by a glutaraldehyde linking group. $^{125}$I-thymosin $\alpha_1$ was used as the probe and was prepared by treatment with Bolton-Hunter reagent. The assay prodecure utilized the double antibody method to achieve separation of the free from bound $^{125}$I-thymosin $\alpha_1$. Soluble goat anti-rabbit gamma globulin was used as the second antibody.

U.S. Patent Application Ser. No. 139,944, now U.S. Pat. No. 4,339,427, filed Apr. 14, 1980 describes a radioimmunoassay for thymosin $\alpha_1$. This assay involves the use of an antibody which has been made more specific to thymosin $\alpha_1$ by heating it with a bovine kidney fraction 5 to remove cross reacting impurities. Radioiodinated[Tyr$^1$]-thymosin $\alpha_1$ is employed as the label.

DESCRIPTION OF THE INVENTION

The present invention relates to an improved immunoassay for thymosin $\alpha_1$. The improvements in such assay involve the use of an antibody having exceptionally good specificity and avidity for thymosin $\alpha_1$. The antibody is elicited using an immunogen which is prepared by coupling [Tyr$^1$]-thymosin $\alpha_1$ to an immunogenic carrier protein using a bifunctional diazonium coupling agent. The [Tyr$^1$]-thymosin $\alpha_1$ which is employed in the preparation of the immunogen corresponds to thymosin $\alpha_1$ in which the N-terminal serine residue has been replaced by a tyrosine residue. We have found that an antibody which is elicited using an immunogen derived from the tyrosyl analog of thymosin $\alpha_1$, in accordance with the teachings of this invention, exhibits a higher degree of avidity and specificity (i.e. lower non-specific binding) when employed in an immunoassay for thymosin $\alpha_1$ than does an antibody similarly derived from thymosin $\alpha_1$ itself.

While the immunoassay of the invention is specifically exemplified herein with respect to an improved radioimmunoassay, it will be understood by those skilled in the art that the improvements described herein are equally applicable to other types of immunoassays involving competitive binding reactions, such as enzymeimmunoassays and fluoroimmunoassays.

A major advantage of the radioimmunoassay described herein is that it employs a relatively short incubation time by comparison with prior art known radioimmunoassays for thymosin $\alpha_1$.

The [Tyr$^1$]-thymosin $\alpha_1$ used in the preparation of the immunogen can be conveniently prepared using solid phase peptide procedures analogous to those employed in the synthesis of thymosin $\alpha_1$ such as is described in the aforementioned U.S. Pat. No. 4,148,788 with the exception that the last amino acid added is tyrosine. The resulting peptide is then treated with an acetylating agent such as acetic anhydride or acetic acid to provide the desired N-terminal acetyl group.

As used herein the term "immunogenic carrier protein" is meant to include those proteins which have the property of independently eliciting an immunogenic response in a host animal and which can be bonded to the [Tyr$^1$]-thymosin $\alpha_1$ through the bifunctional diazonium coupling agent described herein. Accordingly, any proteins which contain side chains which are reactive with the azo groups of the bifunctional diazonium coupling agent are suitable for the purposes of this invention.

Examples of suitable immunogenic carrier proteins include mammalian serum proteins such as, for example, human gamma globulin, human serum albumin, bovine serum albumin, methylated bovine serum albumin, rabbit serum albumin, bovine gamma globulin and equine gamma globulin or non-mammalian proteins such as hemocyanin, particularly keyhole limpet hemocyanin (KLH).

In a preferred embodiment of the invention, the immunogenic carrier protein which is employed in the preparation of the immunogen is a protein which has been treated to impart phenolic groups to the surface of the protein molecule. This can be conveniently achieved by reacting the protein with m-hydroxybenzaldehyde and sodium borohydride using the reaction conditions which are known for the reaction of proteins with simple aldehydes. [Means and Feeney, Biochemistry 7, 2192 (1968)]. Particularly preferred immunogenic carrier proteins in the practice of this invention are bovine serum albumin and keyhold limpet hemocyanin which have been treated in this manner. These are referred to hereinafter as polyphenolic bovine serum albumin (PP-BSA) and polyphenolic keyhole limpet hemocyanin (PP-KLH).

The bifunctional diazonium coupling agent which is employed to couple the immunogenic carrier proteins to the [Tyr$^1$]-thymosin $\alpha_1$ is a compound of the formula Cl$^\ominus$N$\equiv$$^\oplus$N—R—N$^\oplus$$\equiv$N Cl$^\ominus$, wherein R is an organic moiety containing up to about 12 carbon atoms which bridges the two diazonium groups. The organic moiety represented by R may be aromatic or alphatic and it may contain heteroatoms; however, the R moiety preferably does not contain functional groups which are coreactive with the functional groups of either the immunogenic carrier protein or the [Tyr$^1$]-thymosin $\alpha_1$.

Preferably, the bifunctional diazonium coupling agent is a compound containing at least two phenylene moieties in the R group in which each diazonium group, i.e. —⁺N≡N, is bonded directly to a different phenylene moiety.

Exemplary of the bifunctional diazonium coupling agents which can be employed are benzidine-3,3'-dicarboxylic acid, benzidine-2,2'-disulfuric acid, benzidine dihydrochloride, and 3,3'-dimethylbenzidine dihydrochloride. A preferred bifunctional diazonium coupling agent in the practice of the invention is tetrazotized o-dianisidine (TAD), i.e. the compound of the formula

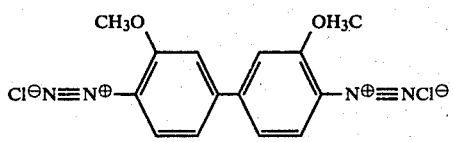

The bifunctional diazonium coupling agent can be prepared from a corresponding diamine compound of the formula $H_2N-R-NH_2$, wherein R has the meaning given above, using known procedures for tetrazotization. For example, o-dianisidine can be converted to TAD by reacting it with $NaNO_2$ in contact with 0.2 M HCl.

In preparing the immunogen, the bifunctional diazonium coupling agent is preferably reacted first with the [Tyr$^1$]-thymosin $\alpha_1$, using a slight molar excess of the coupling agent, and the resulting conjugate is then reacted with the immunogenic carrier protein. Both reactions can be suitably carried out at a temperature from about 0° to 4° C. and a pH of from about 8.8 to 9.0.

The resulting immunogen can be utilized without further purification or, although not necessary, after dialysis to remove any unreacted [Tyr$^1$]-thymosin $\alpha_1$ or bifunctional diazonium coupling agent.

The immunogen of the present invention may be utilized to induce formation of antibodies specific to thymosin $\alpha_1$ in host animals by injecting the immunogen in such a host, preferably using an adjuvant. Improved and stable antibody titers can be obtained by repeated injections over a period of time. Suitable host animals for this purpose include mammals such as rabbits, horses, goats, guinea pigs, rats, cows, sheep, etc. The resulting sera will contain antibodies which will selectively complex with thymosin $\alpha_1$. Due to a high level of homology between the thymosin $\alpha_1$ sequences derived from various mammalian species, it is possible to utilize antibodies raised against one species of thymosin $\alpha_1$ to assay for thymosin $\alpha_1$ of other mammalian species.

The antibodies raised in the manner described above can be employed in any immunoassay for thymosin $\alpha_1$ which employs the principle of competitive binding. In such an assay, a sample containing the unknown amount of thymosin $\alpha_1$ to be measured is reacted with a mixture of antibody specific to thymosin $\alpha_1$ and a standard containing a known concentration of labelled thymosin $\alpha_1$, which label can be quantitatively measured. The label may be, for example, a radioactive label (radioimmunoassay), fluorometric label (fluoroimmunoassay) or an enzymatic label (enzymeimmunoassay). The antibody-antigen complex which forms during this reaction is separated from uncomplexed labelled thymosin $\alpha_1$. The degree of binding of labelled thymosin $\alpha_1$ in the antiobody-antigen complex is measured and the amount of thymosin $\alpha_1$ in the unknown sample is determined by comparing said degree of binding with a standard curve.

A radioimmunoassay performed in accordance with this invention preferably employs [Tyr$^1$]-thymosin $\alpha_1$ or [Tyr$^1$]-desacetylthymosin $\alpha_1$ as the substrate for the radiolabelled probe. While radioiodinated [Tyr$^1$]-thymosin $\alpha_1$ or [Tyr$^1$]-desacetylthymosin $\alpha_1$ are reagents of preference in the radioimmunoassay, it is possible to employ other radiolabelled reagents. Such reagents include [Tyr$^1$]-thymosin $\alpha_1$ or [Tyr$^1$]-desacetylthymosin $\alpha_1$ labelled with tritium ($^3$H) or carbon 14 ($^{14}$C). Tritium can be introduced into such reagents by use of isotopic exchange procedures known in the art. The production of $^{14}$C-[Tyr$^1$]-thymosin $\alpha_1$ or $^{14}$C-[Tyr$^1$]-desacetylthymosin $\alpha_1$ is readily accomplished by incorporating one or more commercially available $^{14}$C-labelled amino acids into the appropriate steps of the solid phase synthesis procedures referenced above.

A preferred method of preparing radioiodinated [Tyr$^1$]-thymosin $\alpha_1$ or [Tyr$^1$]-desacetylthymosin $\alpha_1$ involves reacting the substrate to be labelled with a radioiodide salt such as Na$^{125}$I in an aqueous suspension of lactoperoxidase and glucose oxidase on a solid support such as spheres of a hydrophilic polymer such as cross-linked polycarylamide, which are several microns in diameter. The iodination reaction is initiated by the addition of glucose to the reaction medium. The addition of glucose to the suspension causes the continuous generation of hydrogen peroxide. The lactoperoxidase catalyzes the peroxide oxidation of radioactive iodide to iodine, which reacts with the substrate to produce the $^{125}$I-[Tyr$^1$]-thymosin $\alpha_1$ or $^{125}$I-[Tyr$^1$]-desacetylthymosin $\alpha_1$. Suspensions of lactoperoxidase and glucose oxidase on polymeric spheres are commercially available under the trademark Enzymobead (Bio-Rad Laboratories).

Various assay methods can be employed in the practice of this invention. In one such procedure, known amounts of a sample to be assayed, the thymosin $\alpha_1$ specific antibody and the labelled thymosin $\alpha_1$ are mixed together and incubated. The antibody-antigen complex is separated from the unbound reagents by procedures known in the art, i.e., by treatment with ammonium sulfate, polyethylene glycol, second antibody either soluble or bound to an insoluble support, dextran coated charcoal and the like. The concentration of labelled thymosin $\alpha_1$ is determined in either the bound or unbound phase and the thymosin $\alpha_1$ content of the sample can then be determined by comparing the level of labelled component observed to a standard curve in a manner known per se. A suitable standard curve can be obtained by mixing known amounts of thymosin $\alpha_1$ with fixed amounts of labelled thymosin $\alpha_1$ and the thymosin $\alpha_1$ specific antibody and determining the degree of binding for each such known amount.

In a preferred embodiment of the invention, separation is achieved by the second antibody method wherein the second antibody is bound to the surface of poly(vinylidene fluoride) resin particles in the form of suspended floccules, as described in greater detail in U.S. Pat. No. 3,843,443. As those skilled in the art are aware, the second antibody used in the separation step is generally raised in a host animal which is different from that in which the primary antibody (i.e. anti-thymosin $\alpha_1$) is raised. Thus, for example, if the primary antibody is elicited by inoculating a rabbit with the immunogen, a suitable second antibody for the separation step will be goat anti-rabbit IgG.

The present invention is further illustrated by the following examples.

EXAMPLE 1

Preparation of tetrazotized o-dianisidine (TAD)

A solution of 0.36 g of o-dianisidine dihydrochloride (1 mmole) in 45 ml (0.2 M HCl was cooled in an ice bath. To this was added dropwise (to keep the temperature below 5° C.) a solution of 0.17 g of sodium nitrite (2.46 mmole) in 5 ml distilled water. An orange color formed immediately. The mixture was stirred for another 30 minutes at 4° C. before using.

Preparation of polyphenolic proteins (a) Polyphenolic keyhole limpet hemocyanine (PP-KLH).

One-half ml (50 mg) of keyhole limpet hemocyanin (in 50% glycerol solution) was diluted with 4 ml 0.2 M borate buffer (pH 9.0) and allowed to stand in a refrigerator overnight to dissociate the aggregates of subunits. Dimethylformamide (0.5 ml) was then added and the mixture was placed on an ice bath. A stock solution was prepared by dissolving 0.49 g of m-hydroxybenzaldehyde in 1 ml tetrahydrofuran (warming was necessary). While stirring, 0.15 ml of the m-hydroxybenzaldehyde solution was added to the cold hemocyanin solution. After 5 minutes of mixing, 10 μl of sodium borohydride solution (freshly prepared by dissolving 100 mg in 1 ml distilled water) was added to the protein solution. Further additions were made at 10, 15, 20, and 25 minutes. At 30 minutes the reductive alkylation was halted by the addition of 0.05 ml of glacial acetic acid. The reaction mixture was then dialyzed against 1 liter of distilled water (with one change) for 24 hours followed by 1 liter 0.2 M borate pH 9 buffer for another 24 hours.

(b) Polyphenolic bovine serum albumin (PP-BSA)

The procedure was the same as that for PP-KLH except that 100 mg of BSA was dissolved in 9 ml 0.2 M borate pH 9.0 buffer then mixed with 1 ml dimethylformamide. The subsequent steps were identical to that used for 5 ml KLH solution. After dialysis, spectral analysis (320 nm-240 nm) showed a two-fold increase in the main uv absorption peak.

EXAMPLE 2

Immunogen preparation

To a solution of [Tyr$^1$]-thymosin $\alpha_1$ (5 mg in 1 ml of 0.2 M borate pH 9.0 buffer) placed on ice bath there was added 0.15 ml of cold TAD reagent. The mixture was stirred for 30 minutes (during which time a dard red color appeared).

(a) Coupling with BSA

A solution of 25 mg BSA in 5 ml 0.2 M borate pH 9 buffer was cooled on an ice bath and then mixed with the solution obtained by the reaction of [Tyr$^1$]-thymosin $\alpha_1$ and TAD. The resulting mixture was stirred for 40 hours at 4° C. after which it was dialyzed against 2 liters of 0.9 M NaCl solution for 5 hours at 4° C.

(b) Coupling with KLH

The keyhole limpet hemocyanin solution was prepared for coupling by diluting a 0.22 ml aliquot of the glycerol stock solution in 5 ml of 0.2 M borate pH 9 buffer and letting it stand overnight in the cold. This was then treated with a freshly made solution of conjugate of [Tyr$^1$]-thymosin $\alpha_1$ and TAD in the same manner used to prepare the BSA conjugate.

(c) Coupling with PP-KLH

A solution of 25 mg PP-KLH in 5 ml of the borate buffer was treated with a freshly prepared solution of [Tyr$^1$]-thymosin $\alpha_1$-TAD conjugate in the same manner as with BSA.

EXAMPLE 3

Inoculation of Animals

One ml of the immunogen (PP-KLH conjugate) was diluted with 0.01M phosphate buffered saline at pH 7.0 to 200 μgm/ml(w/v). The dilute immunogen was emulsified in an equal volume of complete Freund's adjuvant. The PP-KLH concentration of the inoculum was 100 μgm/ml. The inoculum was stored at +4° C.

Female rabbits (NZW) weighing 2–2.5 kg were immunized with one ml of inoculum by intradermal injection. The site of injection was rotated from the right to left to right flank. After the initial injection, the rabbits were boosted weekly for four weeks and bi-weekly from then on. The rabbits were bled on a bi-weekly basis after the fifth immunization. The marginal ear vein was lanced, after being swabed with zylene (zylene causes localized vascularization). The blood (40 ml) was allowed to drip freely into a 50 ml conical centrifuge tube which then stood at room temperature for 1 hour (clot formation). To facilitate clot retraction and maximize the serum yield, the tubes were rimmed (mechanically separate the clot from the sides of the centrifuge tube) and stored at 4° C. overnight. The clot was separated from the resulting serum and the red blood cells were pelleted by centrifugation at 2000 rpm for 10 minutes at 4° C. The antibody titer of the serum was determined by radioimmunoassay. The serum was subaliquoted and stored at −20° C. Continued bi-weekly boosting and bleeding maintains an elevated uniform antibody titer and the collection of a large homogeneous antibody pool.

Antibodies can be elicited in a similar manner by inoculating the rabbits with the immunogen prepared using the BSA conjugate or the KLH conjugate.

EXAMPLE 4

Radioiodination of [Tyr$^1$]-thymosin$\alpha_1$

Into a reaction vial containing 1.0 mCi Na$^{125}$I there were added 50 μl 0.2 M phosphate buffer (pH 7.2) with stirring. There were then added with stirring 10 μl [Tyr$^1$]-thymosin $\alpha_1$, followed by 50 μl of an aqueous suspension of lactoperoxidase and glucose oxidase bound to spheres of hydrophilic polymer several microns in diameter (Enzymobeads$^{TM}$, Bio-Rad Laboratories). There were then added 25 μl of 1% aqueous solution of beta-D-glucose with stirring. The reaction was allowed to proceed for 30–45 minutes with periodic stirring. The reaction mixture was removed from the vial with a Pasteur pipet and applied to a 0.9 cm.×18 cm. Sephadex G-10 column. The column was eluted using 10% acetic acid with 0.1% gelatin. The eluate was collected in 10 ml fractions. The $^{125}$I-[Tyr$^1$]-thymosin $\alpha^1$ was in the first peak. The $^{125}$I-[Tyr$^1$]-thymosin $\alpha_1$ was further purified by combining the tubes comprising the first peak from the G-10 column and applying this material to a Sephadex G-50 (0.9 cm.×55 cm.). The column was eluted using 10% acetic acid with 0.1% gelatin. The eluate was collected in 2.5 ml fractions at 4° C. The peak was determined by counting 25 μl aliquots of the fractions in a gamma counter.

EXAMPLE 5

Radioimmunoassay protocol (a) Materials

The buffer used in the radioimmunoassay was prepared by adjusting 0.05 M sodium borate to pH 8.4 with dilute HCl, adding 1 ml 1% thimerosal (merthiolate) and diluting to 1 liter with 0.05 M sodium borate. $^{125}$I-[Tyr$^1$]-thymosin $\alpha_1$, prepared in accordance with Example 4, was diluted to 40,000 cpm/50 $\mu$l with the aforementioned buffer. Standard samples were prepared by diluting synthetic thymosin $\alpha_1$ with buffer to concentrations ranging from 0 pg/0.1ml to 2000 pg/0.1 ml. Rabbit anti-thymosin $\alpha_1$ antibody was elicited using the PP-KLH immunogen described in Example 2. The second antibody employed was goat anti-rabbit IgG which was bound to the surface of suspended poly(vinylidene fluoride) resin particles in the form of floccules.

(b) Procedure

Into a series of tubes there are pipetted 500 $\mu$l aiquots of anti-thymosin $\alpha_1$ at the experimentally determined dilution. Into non-specific background tubes there are pipetted 500 $\mu$l of buffer only. There are then added to the tubes 100 $\mu$l of standard solutions of thymosin $\alpha_1$ or unknown serum samples, with mixing. There are then added 50 $\mu$l of tracer $^{125}$I-[Tyr$^1$]-thymosin $\alpha_1$, with mixing. The tubes are incubated for 24 hours at 4° C. Separation of bound antigen-antibody complex from free tracer is accomplished by adding 1.0 ml of goat anti-rabbit serum immobilized on poly(vinylidene fluoride) to each tube, allowing the tubes to sit at room temperature for 10 minutes and centrifuging the tubes for 10 minutes at 2500–3000 rpm. The supernatants are decanted and the radioactivity in the pellet is counted in a gamma counter for one minute. The counts per minute for standards and unknowns are corrected for non-specific background. An automatic data reduction program utilizing the four-parameter logistics of method of Rodbard, Clin. Chem., 20, 1255 (1974) is used for calculating potency estimates for all samples and for evaluating the performances of the radioimmunoassay from run to run.

It is noted that the procedure employed in the radioimmunoassay of this invention utilizes a single incubation of 24 hours at 4° C., whereas prior art known procedures employ as many as three separate incubations at varying temperatures consuming total incubation time of as much as 66 hours. Thus, the radioimmunoassay of the present invention can be performed more simply and in a shorter period of time.

(c) Results using the RIA for thymosin $\alpha_1$

A standard curve for the RIA was generated using three replicate determinations at each standard concentration. The standard curve indicated that a sensitive system has been generated for the measurement of thymosin $\alpha_1$. The standard curve was obtained by plotting the percent radioactivity bound against concentration of thymosin $\alpha_1$. The values for binding percentage represent the average values for the three replicate determinations at each concentration. Total counts per minute (cpm) of bound radioactivity, i.e. with no competitive binding, were 35,003 cpm. Non-specific binding was 1.63%. Percent radioactivity bound at 0% thymosin $\alpha_1$ concentration was 16.30%. Mid-range concentration was 549.9. Percent radioactivity bound at mid-range was 9.84%. Standard deviation was 46.25 cpm and coefficient of variation was 8.41%.

we claim:

1. In a method for the assay of thymosin $\alpha_1$ in a sample, which method comprises mixing said sample with a known amount of labelled thymosin $\alpha_1$ and an antibody which will selectively complex with said thymosin $\alpha_1$, separating the resulting antibody-antigen complex from uncomplexed labelled thymosin $\alpha_1$, measuring the degree of binding of the said labelled thymosin $\alpha_1$ in said complex and determining the amount of thymosin $\alpha_1$ present in said sample by comparing said degree of binding to a standard curve, the improvement which comprises employing as the antibody therein an antibody which has been elicited in a mammal in response to an immunogen comprising [Tyr$^1$]-thymosin $\alpha_1$ coupled to an immunogenic carrier protein.

2. The improved method of claim 1 wherein said labelled thymosin $\alpha_1$ is $^{125}$I-[Tyr$^1$]-thymosin $\alpha_1$.

3. The improved method of claim 1 wherein said immunogenic carrier protein is bovine serum albumin.

4. The improved method of claim 1 wherein said immunogenic carrier protein is keyhole limpet hemocyanin.

5. The improved method of claim 1 wherein said immunogenic carrier protein is polyphenolic keyhole limpet hemocyanin.

6. The improved method of claim 2 wherein said imunogenic carrier protein is polyphenolic keyhole limpet hemocyanin.

7. The improved method of claim 1 wherein the [Tyr$^1$]-thymosin $\alpha_1$ is coupled to the immunogenic carrier protein with a bifunctional diazonium coupling agent.

8. The improved method of claim 7 wherein said bifunctional diazonium coupling agent is tetrazotized o-dianisidine.

9. The improved method of claim 2 wherein separation of the antigen-antibody complex from uncomplexed labelled thymosin $\alpha_1$ is accomplished by the addition of a second antibody to rabbit anti-thymosin $\alpha_1$ wherein said second antibody is bound to the surface of suspended poly(vinylidine fluoride) resin particles in the form of floccules.

10. The improved method of claim 1 wherein said labelled thymosin $\alpha_1$ is $^{125}$I-[Tyr$^1$]-thymosin $\alpha_1$, said immunogenic carrier protein is polyphenolic keyhole limpet hemocyanin and the immunogenic carrier protein is coupled to the [Tyr$^1$]-thymosin $\alpha_1$ with tetrazotized 0-dianisidine.

11. An immunogen for eliciting antibody production which comprises [Tyr$^1$]-thymosin $\alpha_1$ coupled to an immunogenic carrier protein.

12. An immunogen as claimed in claim 11, wherein said [Tyr$^1$]-thymosin $\alpha_1$ is coupled to said immunogenic carrier protein through a bifunctional diazonium coupling agent.

13. An immunogen as claimed in claim 11, wherein said [Tyr$^1$]-thymosin $\alpha_1$ is coupled to said immunogenic carrier protein through tetrazotized o-dianisidine.

14. An immunogen as claimed in claim 13, wherein said immunogenic carrier protein is polyphenolic keyhole limpet hemocyanin.

15. An immunogen as claimed in claim 13, wherein said immunogenic carrier protein is polyphenolic bovine serum albumin.

16. An antibody to thymosin $\alpha_1$ which is elicited in a mammal in response to an immunogen comprising [Tyr$^1$]-thymosin $\alpha_1$ coupled to an immunogenic carrier protein.

* * * * *